US006500138B1

(12) United States Patent
Irby et al.

(10) Patent No.: US 6,500,138 B1
(45) Date of Patent: Dec. 31, 2002

(54) ELECTROMECHANICAL JOINT CONTROL DEVICE WITH WRAP SPRING CLUTCH

(75) Inventors: Steven E. Irby, Rochester, MN (US); Kenton R. Kaufman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/545,420

(22) Filed: Apr. 7, 2000

(51) Int. Cl.⁷ .................................................. A61F 5/00
(52) U.S. Cl. ........................... 602/26; 623/24; 623/44; 623/45
(58) Field of Search ............................. 602/26; 623/24, 623/39, 40, 42, 43–45

(56) References Cited

U.S. PATENT DOCUMENTS

| | | | |
|---|---|---|---|
| 4,711,242 A | * 12/1987 | Petrofsky | 602/1 |
| 4,760,903 A | 8/1988 | Stegelmeier et al. | |
| 4,953,543 A | * 9/1990 | Grim et al. | 602/16 |
| 5,052,379 A | 10/1991 | Airy et al. | |
| 5,112,296 A | * 5/1992 | Beard et al. | 128/905 |
| 5,133,437 A | * 7/1992 | Larson | 192/12 BA |
| 5,251,735 A | * 10/1993 | Lamoureux | 192/35 |
| 5,318,161 A | * 6/1994 | Lyga | 192/107 T |
| 5,484,389 A | * 1/1996 | Stark et al. | 482/8 |
| 5,980,435 A | * 11/1999 | Joutras et al. | 482/114 |
| 6,119,841 A | * 9/2000 | Orlamunder | 192/55.61 |

FOREIGN PATENT DOCUMENTS

| | | | | |
|---|---|---|---|---|
| GB | WO 94/09727 | * 5/1999 | | A61F/2/68 |
| WO | WO 94/09727 | 5/1994 | | |
| WO | WO 97/00661 | 1/1997 | | |

OTHER PUBLICATIONS

K. R. Kaufman, S.E. Irby, J.W. Mathewson, R.W. Wirta, D.H. Sutherland; Energy–Efficient Knee–Ankle–Foot Orthosis: A Case Study. Summer 1996, Journal of Prosthetics and Orthotics, vol. 8, No. 3. p. 80.*
Irby, et al., *IEEE Transactions on Rehabilitation Engineering*, 1999, 7(2):130–134.
Irby, et al., *IEEE Transactions on Rehabilitation Engineering*, 1999, 7(2):135–139.
Kaufman, et al., *Journal of Prosthetics and Orthotics*, 1996, 8(3):79–85.
Kaufman, et al., "Advanced Design Concepts for A Knee–Ankle–Foot Orthotics," Chapter X, pp. 1–23.
Malcolm, et al., "A Digital Logic Controlled Electromechanical Orthosis for Free Knee Gait in Muscular Dystrophic Children," 26$^{th}$ Annual ORS, Atlanta, Georgia, Feb. 5–7, 1980.
McGhee, et al., *IEEE Transactions on Biomedical Engineering*, 1978, BME–25(2):195–199.
Wiebusch, "The Spring Clutch," *J. Applied Mechanics*, pp. 47–52.

* cited by examiner

Primary Examiner—Corrine McDermott
Assistant Examiner—William H Matthews
(74) Attorney, Agent, or Firm—Fish & Richardson P.C., P.A.

(57) ABSTRACT

A clutch including an output hub on an output frame, an input shaft on an input frame, wherein the input shaft rotates within a bore in the output hub. An input hub is attached on an end of the input shaft, and a spring engages the input hub and the output hub. A locking spring clamp attaches the spring to the input hub. The input frame and the output frame are adjacent to one another on a side of the clutch opposite the input hub. An electronic control system for the clutch is also described that makes possible the use of the apparatus for electromechanical joint control in an orthotic or prosthetic device.

33 Claims, 10 Drawing Sheets

- - - - - Knee Joint Angle
———— Footswitch Input
— - — Control Circuit Activated

ELECTROMECHANICAL JOINT CONTROL DEVICE WITH WRAP SPRING CLUTCH

STATEMENT REGARDING FEDERALLY SPONSORED RESEARCH AND DEVELOPMENT

The U.S. Government has a paid-up license in this invention and the right in limited circumstances to require the patent owner to license others on reasonable terms as provided for by the terms of contract number R01HD30150 awarded by the National Institute of Health (NIH).

TECHNICAL FIELD

This invention relates to a dynamic electromechanical orthotic or prosthetic device with a wrap spring clutch.

BACKGROUND

Many amputees and patients with partial or complete paralysis of the extremities require assistive technology such as, for example, prostheses or orthoses, respectively (referred to herein by the general term orthosis or orthotic device), to enhance mobility.

For example, to function efficiently, the lower extremity should have the ability to: (1) support body weight during the stance phase of the locomotion cycle (when the foot is in contact with the ground); (2) rotate and coordinate the joints to achieve forward progression; (3) adjust limb length by flexing the knee during the swing phase of gait (when the foot is not in contact with the ground); and (4) further smooth the trajectory of the center of gravity by slightly flexing the knee in mid-stance.

Figure 1:
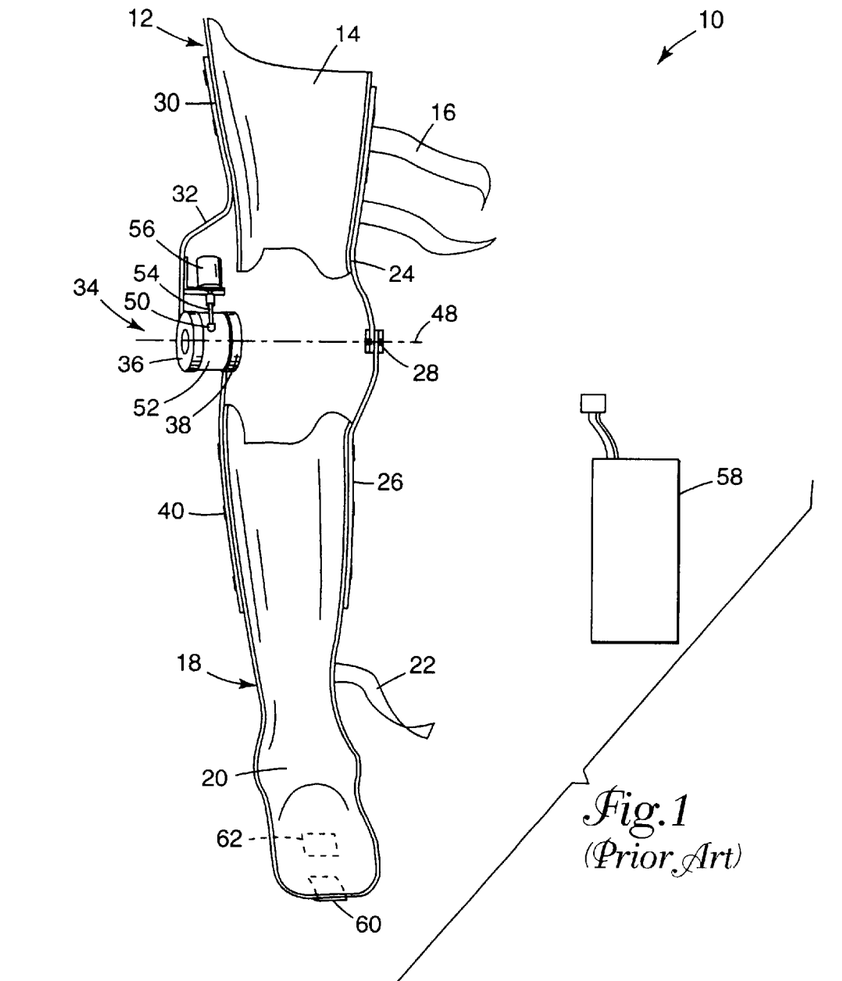
FIG. 1 is a schematic frontal perspective view of a knee-ankle-foot orthosis (KAFO).

To provide efficient locomotion, a knee-ankle-foot orthotic (KAFO) must restrain knee joint flexion at heel strike through the stance phase of the gait while also permitting free knee flexion during the gait swing phase. KAFOs with electromechanical knee restraint components utilize a wide variety of electronically controlled mechanical clutch and brake designs to provide knee control during walking. One successful design includes a small, lightweight, electronically controlled knee lock mechanism that can be installed on a conventional KAFO. Referring to FIG. 1, the KAFO device 10 includes an orthotic with an upper portion 12 with a thigh cuff 14 and thigh retaining straps 16, as well as a lower portion 18 with a lower leg/foot cuff 20 and corresponding foot retaining straps 22. A medial thigh strut 24 and a medial shank strut 26 are connected by a conventional hinge 28 at the knee joint on the medial side of the device 10. On the lateral side of the device, a lateral thigh strut 30 connects to the thigh cuff 14 and extends outwardly at a bend 32 to engage the output hub 38 of a knee hinge clutch mechanism 34. The input hub 36 of the clutch mechanism 34 is connected to a generally straight lateral shank strut 40 joined to the lower leg/foot cuff 20.

Figure 2:
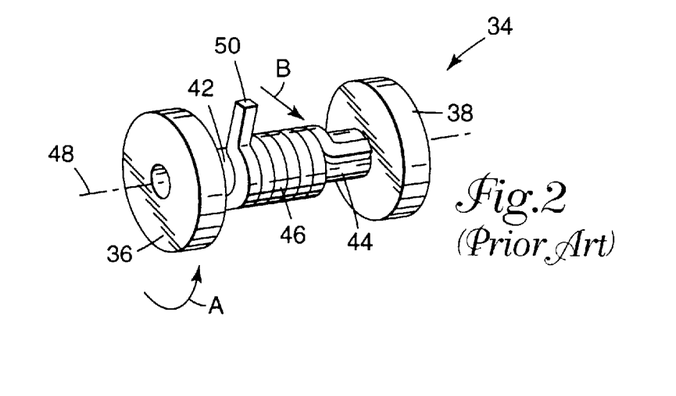
FIG. 2 is a schematic perspective view of a conventional wrap spring clutch mechanism.

Referring to FIG. 2, the clutch mechanism 34 is a wrap spring clutch. Wrap spring clutches are a known class of overrunning clutches that allow torque to be transmitted from one shaft to another in only one direction of rotation. The clutch mechanism 34 includes a cylindrical input arbor 42 attached to the input hub 36, a cylindrical output arbor 44 attached to the output hub 38, and a cylindrical spring 46 having turns with a substantially square cross sectional shape. The input arbor 42 and the output arbor 44 are the same diameter and maintained end-to-end in an abutting relationship by a retaining clip (not shown), and rotate on a common axis. This rotational axis, referred to herein as the flexion extension axis 48, is collinear with respect with the rotational axis of the medial hinge 28 (See FIG. 1). The spring 46 is connected to the output arbor 44, slips on the input arbor 42 and acts as self-engaging brake between them. If a torque is applied to the input hub 36 in the direction of arrow A, the spring 46 wraps down tightly onto the shaft formed by the abutting input arbor 42 and the output arbor 44, which locks the input arbor 42 and the output arbor 44 together and locks the lateral electromechanical knee joint. Conversely, when torque is applied in a direction opposite arrow A, the spring 46 unwraps from the shaft formed by the input arbor 42 and the output arbor 44, which permits the shaft to slip easily in the opposite direction and allows the electromechanical knee joint to swing freely. If the input arbor 42 and the output arbor 44 are under load and must be disengaged, a control tang 50 on the spring 46 may be moved in the direction of arrow B to release the spring 46.

Referring again to FIG. 1, a circumferential control collar 52 around the spring 46 engages the control tang 50. The control collar 52 is engaged via a turnbuckle 54 attached to the output member of an electrically actuated linear solenoid 56 mounted on the lateral thigh strut 32. The linear solenoid 56 is controlled by an electronic control system 58 attached to the belt of the wearer. The control system 58 receives electrical input signals from an arrangement of two sets of foot contact sensors and, based on these signals, generates electrical output signals to control the solenoid 56. The first set of sensors 60, 62 are force sensitive resistors mounted on the underside of the lower leg/foot cradle 20, and provide varying electrical input signals to the control module 58 dependent on the degree of contact between the cradle 20 and a walking surface. The second sensors are attached on the underside of the wearer's opposite foot (not shown in FIG. 1) and provide varying electrical input signals to the control module 58 dependent on the degree of contact between the opposite foot and the ground. A combination logic network in the electronic control module 58 monitors electrical output commands based on the inputs from the foot sensors on the orthotic and the opposite foot. Based on the input from the sensors, a controller algorithm generates an actuation signal that is sent to the solenoid 56 for release of the clutch mechanism 34 during the swing phase of the gait.

The prosthetic/orthotic device 10 shown in FIGS. 1–2 provides an articulated knee joint system that reduces metabolic energy requirements during gait. The locking action of the clutch 34 provides knee stability during stance while allowing free knee motion during the swing phase of gait.

SUMMARY

The orthotic device illustrated in FIGS. 1-2 provides significantly enhanced performance compared to a conventional fixed knee orthosis. However, the extremely wide lateral profile of the clutch 34 makes the device 10 unattractive and difficult to wear under clothing such as trousers or skirts. In addition, the offset between the lateral thigh strut 30 and the lateral shank strut 40 increases torsional loading at the joint compared to conventional in-line braces. The foot sensors attached to both the device 10 and the opposed foot of the wearer are both unattractive and inconvenient to connect/disconnect.

The invention provides a wrap spring clutch with a significantly reduced lateral profile, which makes an orthotic device using the clutch much more attractive to wear under clothing. The reduced lateral profile and adjacent input/ output frames of the clutch also reduce torsion in the lateral knee joint region. The wrap spring clutch provides bidirectional rotation, multiple locking positions, self-engagement and simple disengagement under load with very little energy input from a power source such as a battery. The wrap spring clutch design also provides a fail-safe locking mechanism if power fails. The low profile clutch design makes the device easy to use, and, consequently, more patients requiring the assistance of an orthotic device would be more likely to actually wear it on a daily basis. The unilateral input from sensors on the orthotic device renders unnecessary the extra set of wires and sensors that previously encumbered the wearer's contralateral foot, and also greatly simplifies attachment and removal of the device.

In one aspect, the invention is a clutch including an output hub on an output frame, and an input shaft on an input frame, wherein the input shaft rotates within a bore in the output hub. An input hub is attached on an end of the input shaft, and a spring engages the input hub and the output hub. A circumferential spring clamp secures the spring to the input hub such that the input frame and the output frame are adjacent to one another on a side of the clutch opposite the input hub.

In another aspect, the invention is an orthotic joint control apparatus, including a clutch with an output hub on an output frame and an input shaft on an input frame, wherein the input shaft rotates within a bore in the output hub. An input hub is attached on an end of the input shaft, a spring engaging the input hub and the output hub, and a circumferential spring clamp secures the spring to the input hub. The input frame and the output frame are adjacent one another on a side of the clutch opposite the input hub. A first strut is attached to the input frame a second strut is attached to the output frame.

In a third aspect, the invention is a knee-ankle-foot orthotic device, including:
 (a) a medial thigh strut and a medial shank strut, wherein the medial thigh strut and the medial shank strut are attached at a hinge rotating about a flexion extension axis;
 (b) a lateral thigh strut and a lateral shank strut, wherein the lateral thigh strut and the lateral shank strut are attached to a wrap spring clutch rotating about the flexion extension axis;
 (c) a first orthotic member adapted to engage the thigh, wherein a medial side of the first orthotic member is attached to the medial thigh strut and a lateral side of the first orthotic member is attached to the lateral thigh strut;
 (d) a second orthotic member adapted to engage at least one of the lower limb and foot, wherein a medial side of the second orthotic member is attached to the medial shank strut and a lateral side of the second orthotic member is attached to the lateral shank strut;
 (e) an electrically actuated device attached to one of the first and second lateral struts, wherein said electrically activated device, when activated, disengages the clutch;
 (f) contact sensors attached to an underside of the second orthotic member and acted upon by a walking surface, wherein the contact sensors generate an electrical signal corresponding to the degree of contact between the second orthotic member and the surface;
 (g) a kinematic sensor generating an electrical signal based on the relative position and/or movement of the input frame with respect to the output frame; and
 (h) electronic circuitry receiving electrical input signals from the contact sensors and the kinematic sensors, and generate electrical output signals to actuate the electrically actuated device.

In a fourth aspect, the invention is a process for electromechanically controlling the knee joint, including:
 (a) providing a prosthetic device comprising a thigh strut and a shank strut, wherein the thigh strut and the shank strut are attached to a wrap spring clutch rotating about a flexion extension axis; a first prosthetic member adapted to engage the thigh, wherein the first prosthetic member is attached to the thigh strut, and a second prosthetic member attached to the shank strut; and
 activating the clutch using electrical input signals generated by at least one contact sensor on the second prosthetic member and electrical input signals generated by a kinematic sensor corresponding to the relative position and/or movement of the first and second prosthetic members.

In a fifth aspect, the invention is a process for electromechanically controlling a knee joint in an orthotic device, including:
 (a) providing an orthotic device comprising a thigh strut and a shank strut, wherein the lateral thigh strut and the lateral shank strut are attached to a wrap spring clutch rotating about a flexion extension axis; a first orthotic member adapted to engage the thigh, wherein the first orthotic member is attached to the thigh strut, and a second orthotic member adapted to engage at least one of the lower limb and foot, wherein a the second orthotic member is attached to the shank strut; and
 activating the clutch using electrical input signals generated by at least one contact sensor on the second orthotic member and electrical input signals generated by a kinematic sensor corresponding to the relative position and/or movement of the first and second orthotic members.

In a sixth aspect, the invention is a process for electromechanically controlling a joint in an orthotic device, including:
 (a) providing an orthotic device comprising a first strut and a second strut, wherein the first strut and the second strut are attached to a wrap spring clutch rotating about a flexion extension axis; a first orthotic member attached to the first strut a second orthotic member attached to the second strut; and
 activating the clutch using electrical input signals generated by at least one contact sensor on the second orthotic member and electrical input signals generated by a kinematic sensor corresponding to the relative position and/or movement of the first and second orthotic members.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 3:
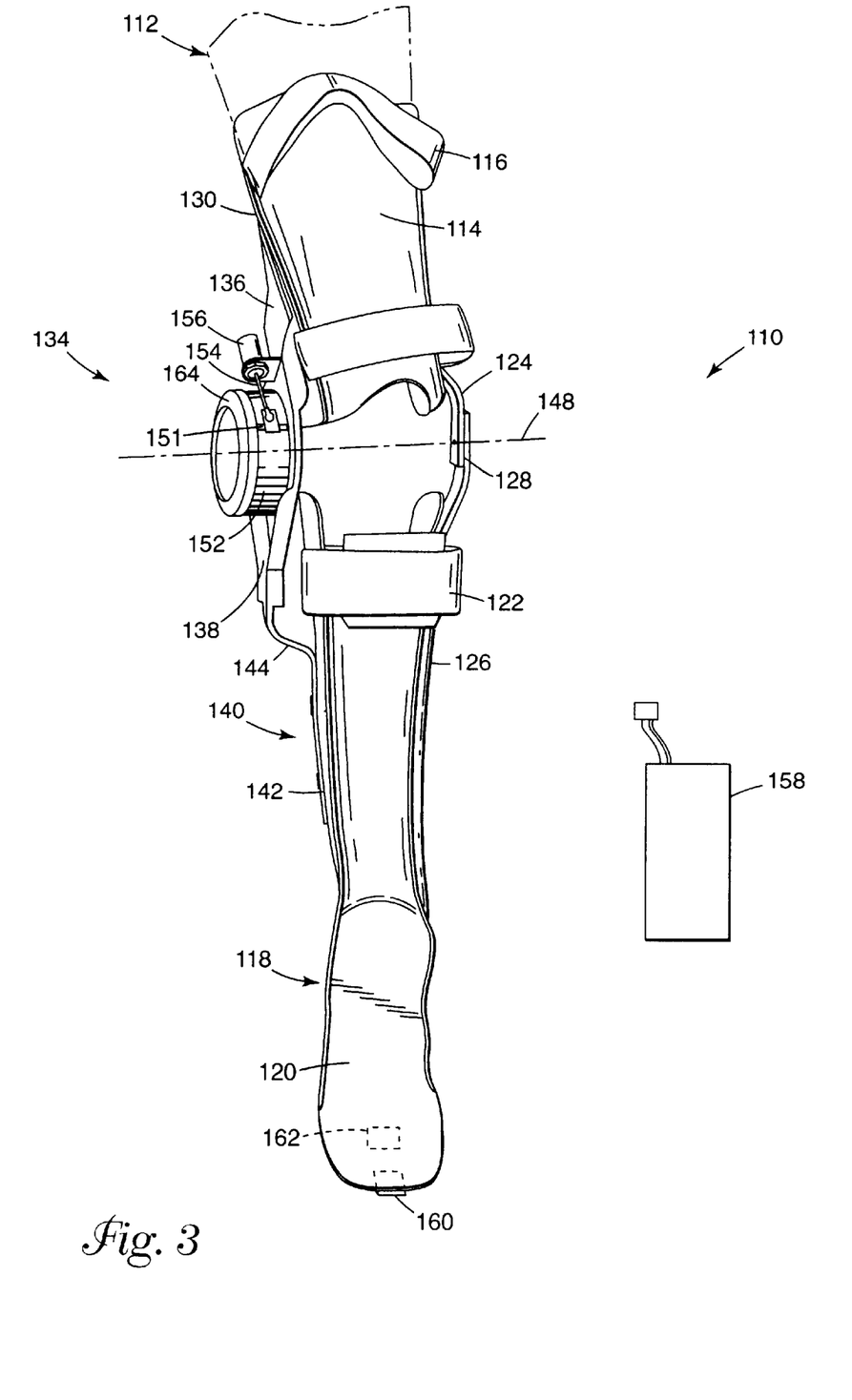
FIG. 3 is front perspective view of an orthotic device of the invention.

An embodiment of an orthotic device 110 of the invention is shown in FIG. 3. The device 110 includes an upper portion 112 with a first orthotic member 114 and thigh straps 116 for attaching the device to an upper leg of a wearer. A lower portion 118 of the device 110 includes a second orthotic member 120 shaped to support the lower leg and/or foot of the wearer, along with a shank strap 122 for attachment of the device to the lower extremity. A medial thigh strut 124 attaches to the medial side of the first orthotic member 114, and a medial shank strut 126 attaches to the medial side of the second orthotic member 120. A conventional hinge 128 rotating about a knee flexion/extension axis 148 connects the medial thigh strut 124 and the medial shank strut 126. A substantially linear lateral thigh strut 130 is attached to an input frame 136 of a wrap spring clutch mechanism 134. A lateral shank strut 140 includes a substantially linear lower portion 142 and an arcuate upper portion 144 connected to an output frame 138 of the clutch 134. The input frame 136 and the output frame 138 are adjacent to one another and are both positioned on the medial side of the clutch mechanism 134, which creates a reduced lateral profile compared to a clutch mechanism with one input member on the medial side of the clutch and one output members on the lateral side of the clutch. Since the input frame 136 and the output frame 138 are adjacent to one another and substantially aligned, the clutch 134 of the invention also reduces torsional forces applied to the orthosis.

The input frame 136, the output frame 138, and other components of the clutch mechanism at typically made of a lightweight metal such as, for example, aluminum, to reduce the overall weight of the orthotic device. However, any metal would be suitable for use in making the clutch components, and, for example, steel may be used for all or part of the components if weight is not a significant concern or if enhanced durability is required.

A turnbuckle member 154 acts on a split yoke 151 on an external surface of a circumferential control collar 152 retained by a circumferential locking spring clamp 164. The turnbuckle member is actuated by the output member of an electromechanical actuation device 156 mounted on the lateral thigh strut 132. The actuation device, in this embodiment a linear solenoid 156, is controlled by an electronic control system 158 that may be attached to the belt of the wearer or mounted on medial or lateral thigh struts 124, 130. The control system 158 receives electrical input signals from a single set of foot contact sensors and, based on these signals, generates electrical output signals to control the solenoid 156. The sensors 160, 162 are force sensitive resistors mounted on the underside of the second orthotic member 120, and provide varying electrical input signals to the control module 158 dependent on the degree of contact between the second member 120 and a walking surface. No sensors on the underside of the wearer's contralateral foot are required. Electronic circuitry 158 monitors electrical output commands based on the inputs from the foot sensors 160,162 on the device 110. Based on the input from the sensors, a controller algorithm generates an actuation signal that is sent to the solenoid 156 for release of the clutch mechanism 134 during the swing phase of the gait.

Figure 4:
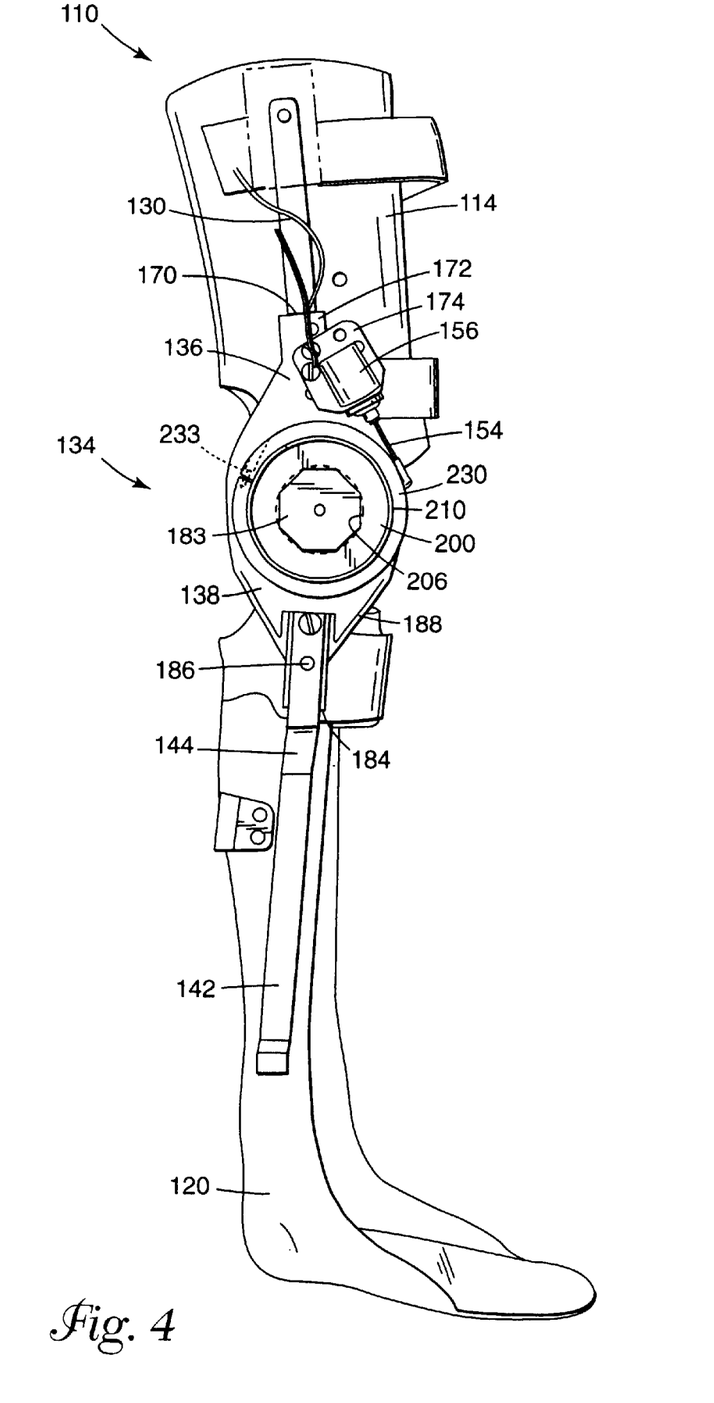
FIG. 4 is a side view of an orthotic device of the invention.
Figure 5:
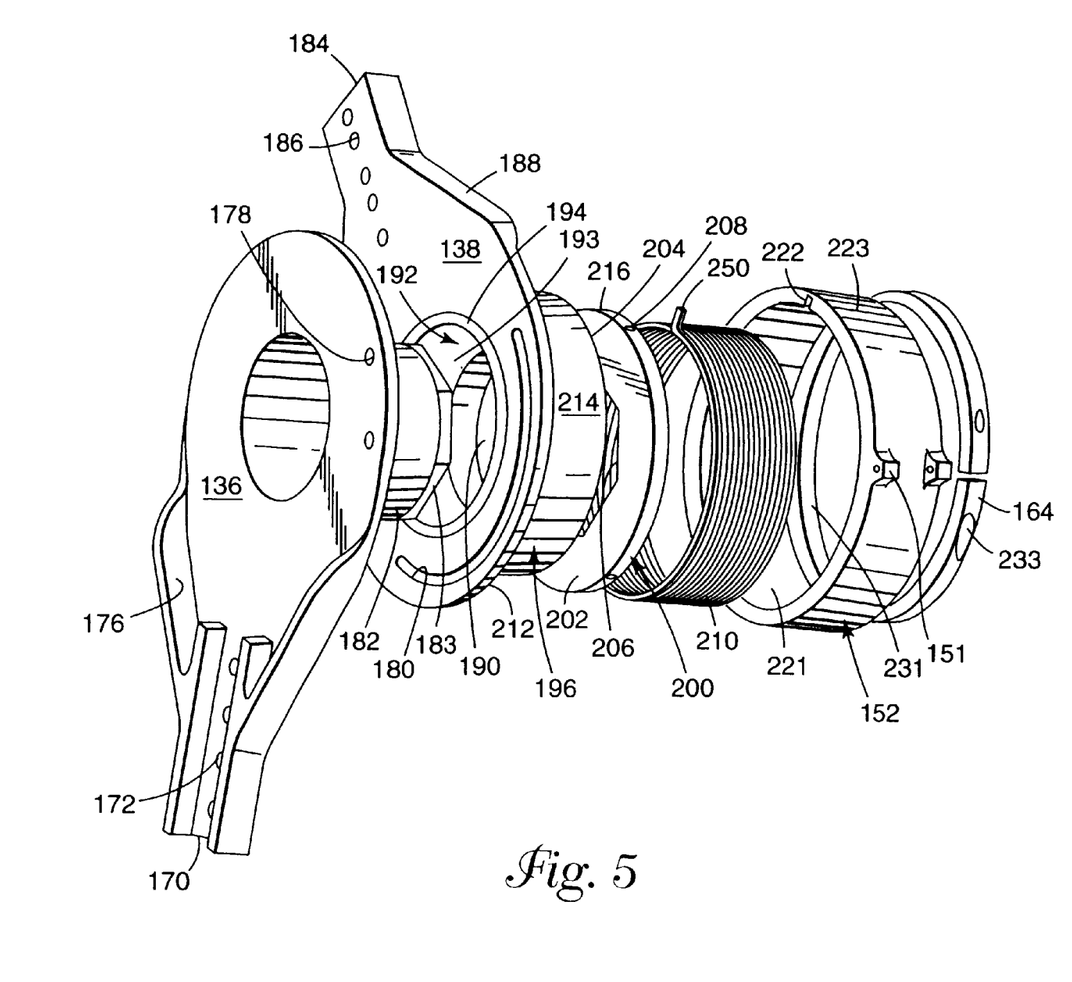
FIG. 5 is an exploded perspective view of the wrap spring clutch of the invention.

Referring to FIGS. 4–5, the input frame 136 is a substantially planar member that typically includes an elongate linear connection portion 170 for attachment of the clutch to strut of an orthotic device. However, the elongate portion 170 may be out of plane if necessary to more closely parallel the profile of a typical orthotic device. The connection portion 170 includes a series of mounting apertures 172 to provide adjustable attachment to the lateral thigh strut 130. The mounting apertures may also be used to mount a bracket 174 for the solenoid 156, or to mount a battery pack or the electronic control module 158 (not shown in FIGS. 4–5). The connection portion 170 of the input frame 136 includes reinforcing flanges 176, as well as a pair of peripheral apertures 178. The apertures 178 are typically used to retain set screws or similar stop members (not shown in FIGS. 4–5) to engage a circumferential groove 180 in the output frame 138 limit the rotation of the input frame 136 with respect to the output frame 138 and prevent hyperextension of the knee joint. The input frame 136 further includes an input arbor or input shaft 182 having a longitudinal axis generally normal to the plane of the input frame 136 and collinear with the flexion/extension axis 148 (See FIG. 3).

The output frame 138 is also a substantially planar member that includes an elongate linear connection portion 184. The connection portion 184, which also may be out of plane if necessary to connect to a strut of an orthotic device, includes a series of mounting apertures 186 for adjustable attachment of the output frame 138 to the arcuate portion 144 of the. lateral shank strut 142. Reinforcing flanges 188 stiffen the connection portion 184 and extend in a direction opposite to the reinforcing flanges 176 on the input frame 136. The input arbor 182 is received in a bore 190 in the output frame 138 and is free to rotate therein. The input arbor 182 rotates in the bore 190 on at least one flanged sleeve bearing 192. The bearing 192 has a sleeve portion 193 in the bore 190 and a circumferential flange portion 194 between the adjacent input frame 136 and the output frame 138. The input arbor 182 is retained concentrically within an output hub 196 having a longitudinal axis generally normal to the plane of the output frame 138.

An end 183 of the input arbor 182 extends beyond the output hub 196 and is attached to an input hub 200. The input hub 200 has substantially the same diameter as the output hub 196 and includes a substantially planar engagement surface 202 that abuts against a substantially planar engagement surface 204 on the output hub 196. The end 183 of the input arbor 182 is machined with a substantially octagonal cross sectional shape, although other similar shapes and/or splined arrangements may be used. The machined portions on the input arbor 182 have substantially parallel faces that engage a corresponding octagonally shaped interior attachment surface 206 of the input hub 200. A radial set screw 208 in the input hub 200 may be used to ensure reliable engagement of the input arbor 182 and the input hub 200.

Figure 6:
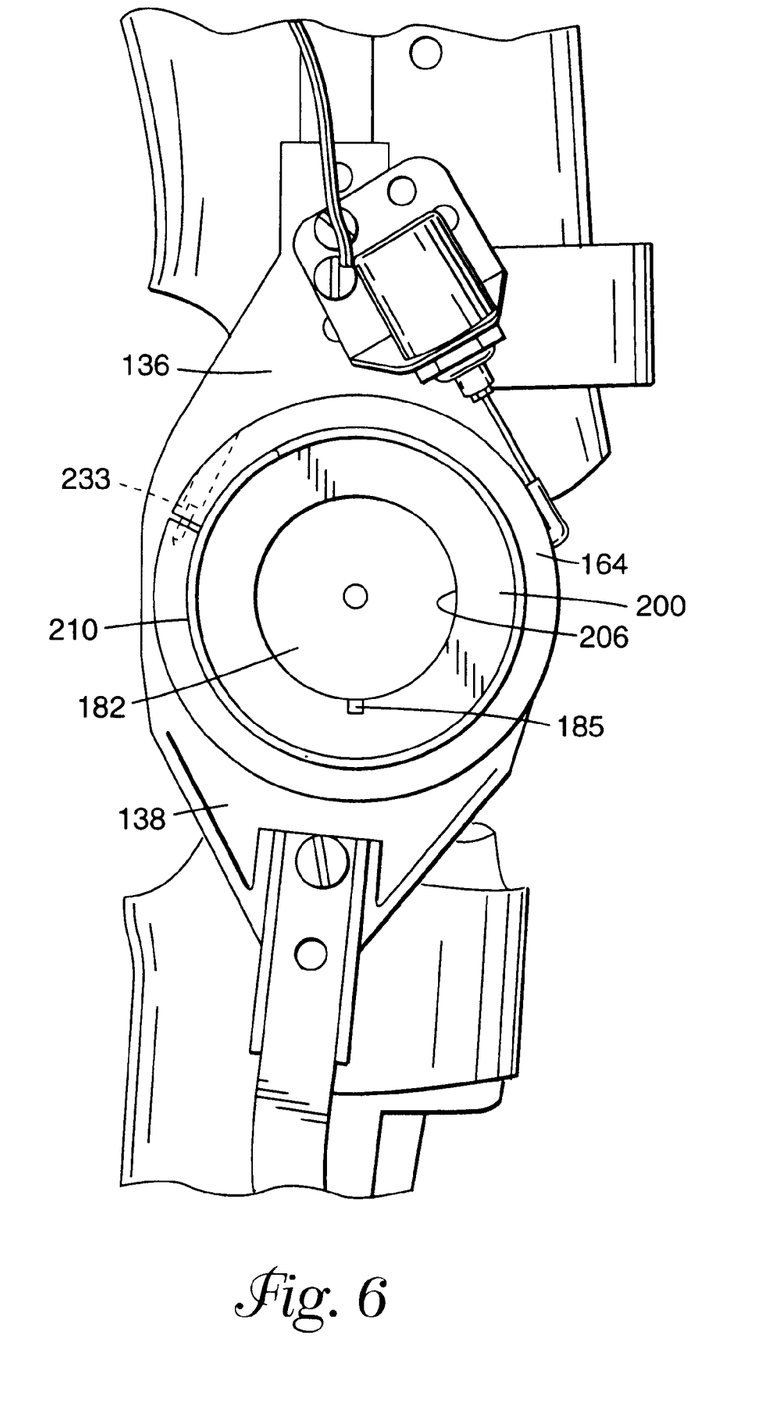
FIG. 6 is a detailed side view of an embodiment of the clutch of the invention.

In an alternative embodiment illustrated in FIG. 6, the end 183 of the input arbor 182 has a substantially circular cross sectional shape. A longitudinal keyway may be machined in the distal end 183 of the input arbor 182 to accept a flat key 185. The interior surface 206 of the input hub 200 also has a circularly shaped interior attachment surface 206. A radial set screw (not shown in FIG. 6) in the input hub 200 may be used to retain the key 185 and maintain engagement with the input arbor 182.

A substantially cylindrically shaped helical spring 210, which has a diameter slightly smaller than the diameters of the output hub 196 and the input hub 200, is forced over the output hub 196 and the input hub 200. The spring 210, which is preferably fabricated with wire having a substantially square or rectangular cross sectional shape, frictionally engages an exterior surface 214 of the output hub 196 and an exterior surface 216 of the input hub 200. To provide a more stable friction surface, the exterior surface 214 of the output hub 196 and the exterior surface 216 of the input hub 200 may be sleeved or coated with a hardened or wear resistant material such as, for example, steel.

As noted above, a torque is applied to the clutch 134 will tend to rotate the input frame 136, the input arbor 182 and the input hub 200 with respect to the output hub 196. If the torque is applied to the input frame 136 and the input hub 200 in a first direction so as to wind the spring 210 down in the hubs, maximum torque is transmitted by the clutch 134. If the torque is applied in a second direction opposite the first direction so as to unwind the spring 210, minimal torque is transmitted to the output hub 196 by the clutch 134.

Referring again to FIGS. 3–5, the spring 210 is engaged by an interior surface 221 of a circumferential control collar 152, which slips over the spring 210 and rests against the shoulder 212 on the output frame 138. The control collar 152 includes a longitudinal notch 222 that retains a control tang 250 in the spring 210. If the clutch 134 is under load and must be disengaged, the control collar may be rotated about the spring 210. The notch 222 pushes the tang 250 in the second direction so as to unwrap the spring 210 and disengage the clutch 134. An outer surface 223 of the control collar 152 includes a split yoke 151 to make possible the circumferential movement of the control collar (See FIG. 7).

The control collar 152 is maintained in position abutting the shoulder 212 by a circumferential spring clamp 164. If the tangential set screw 233 is tightened, the interior engagement surface 231 of the spring clamp 164 also locks the spring 210 to the input hub 200.

Figure 7:
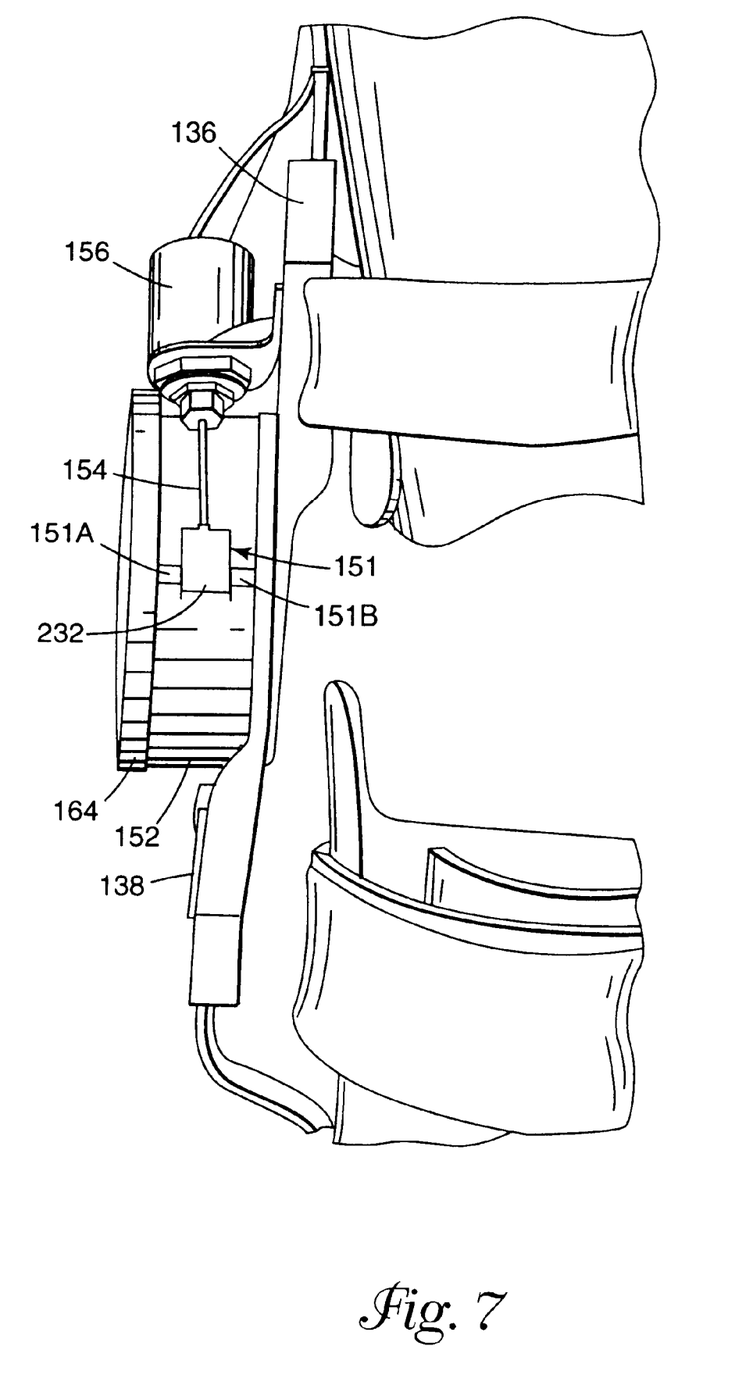
FIG. 7 is a front detailed view of an orthotic device of the invention.

Referring to FIG. 7, the control collar 152 is moved circumferentially about the spring 210 by an electrically actuated linear solenoid 156. When the solenoid 156 is energized, the solenoid shaft (not shown in FIG. 7) displaces the turnbuckle member 154, which is adjustable in its linear dimensions to control the action of the collar 152 on the spring tang 250. The turnbuckle member 154 acts on a clevis member 232, which translates the linear action of the member 154 into circumferential movement of the collar 152. The clevis member 232 resides within the two posts 151A, 151B of the split yoke 151 and engages a linear pin (not shown in FIG. 7) extending between the posts 151A, 151B.

The control inputs for the solenoid 156, which disengages the clutch 134, are derived from naturally occurring gait events. The timing and repeatability of these events are critical to a successful application. The chronology of foot contact events, as they relate to gait kinematics and kinetics, was used to guide the control system design.

Figure 8:
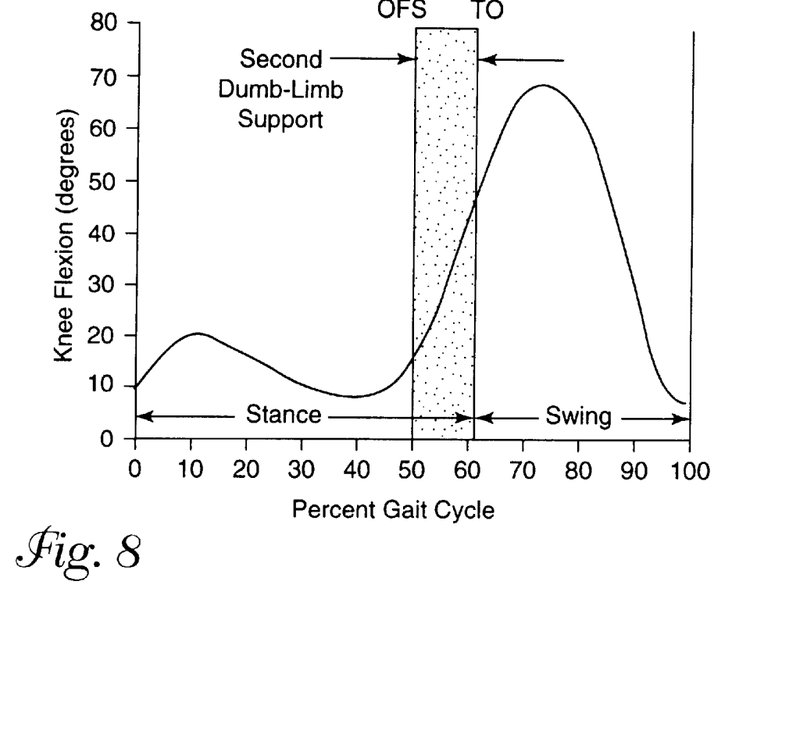
FIG. 8 is a plot of normal sagittal knee motions in degrees of knee flexion vs. percent gait cycle.
Figure 9:
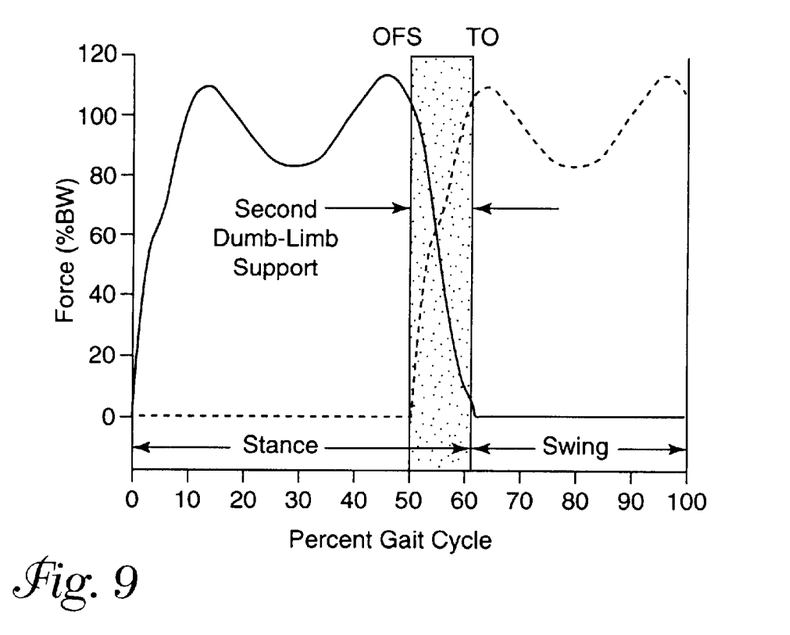
FIG. 9 is a plot of normal foot floor contact forces perpendicular to the floor plane in force, normalized to percent of body weight, vs. percent gait cycle.

Referring to FIGS. 8–9, kinematic and kinetic gait parameters are normalized in time to 100% of a gait cycle. The stance phase of a gait cycle begins at 0% with foot contact. For a normal individual, opposite foot strike (OFS) occurs at 50% of the gait cycle. The opposite limb begins to accept the weight of the individual in preparation for advancement of the trailing limb. Stance phase ends and swing phase begins with toe off (TO) at approximately 62% of the gait cycle. Swing phase is terminated at foot strike, or 100% of the gait cycle. Knee joint engagement must occur after peak knee flexion is attained during swing phase, but no later than foot strike (FIG. 8). The clutch 134 can be engaged any time after peak knee flexion in swing because extension is possible at all times due to the over-running capability of the wrap spring clutch design.

Referring to FIG. 9, the dashed line represents opposite limb forces. Normal timing of opposite foot strike (OFS) and toe-off (TO) bound the critical time period for knee joint control. The solenoid 156 must be activated to disengage the clutch 134 after sufficient weight transfer has occurred. That is, after OFS but prior to TO, in order for sufficient knee flexion to occur and to obtain foot clearance during the swing phase of gait. The high rate of loading at the onset of stance creates an inviolable constraint lest the knee collapse into flexion. Disengagement must occur after sufficient weight transfer to the opposite leg has taken place (after opposite foot strike), but soon enough to allow the knee to flex before toe-off (FIG. 8). Thus, there is a narrow time window in which the clutch must be activated.

In view of the above, if information regarding: (1) the contact between the second orthotic member 120 (FIG. 3) with respect to a walking surface, and (2) knee flexion or joint angle input, i.e. the respective rotational displacement and/or velocity of the input frame 136 with respect to the output frame 138, is obtained and transmitted to the solenoid 156, the clutch 134 may be disengaged and engaged in a timely manner to closely approximate a natural gait cycle.

Figure 10:
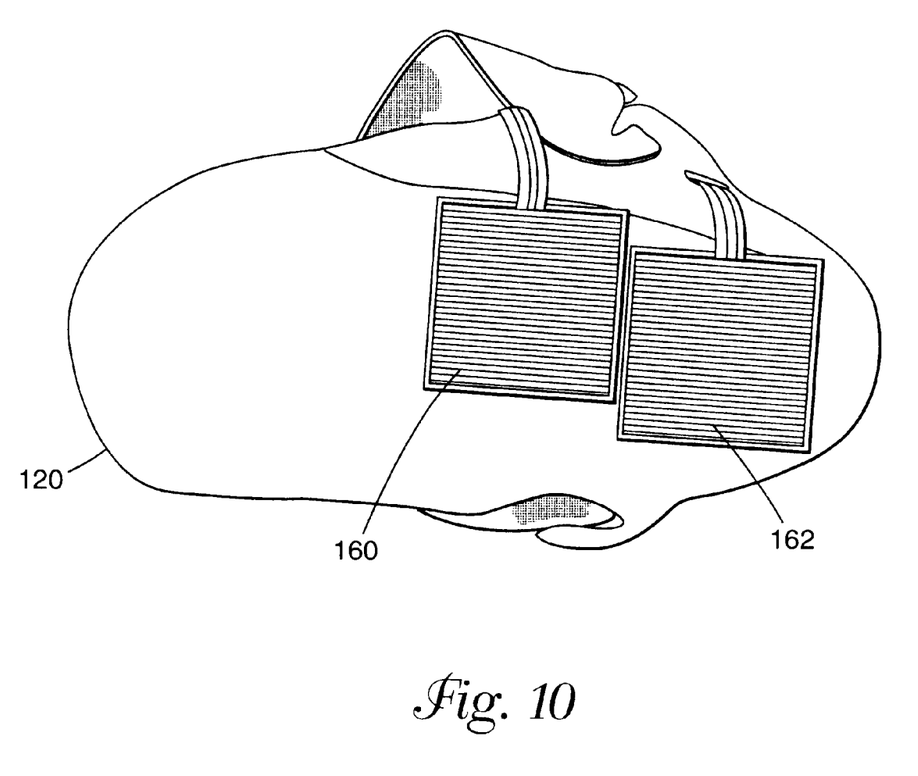
FIG. 10 is a view from beneath the orthotic showing placement of a pair of force sensitive sensors.

Referring to FIG. 10, information regarding heel strike and toe-off may be obtained with a pair of sensors 160, 162 placed on a the second orthotic member 120, which will be acted upon by the walking surface. The sensors 160, 162 are typically force sensitive resistive elements that provide variable resistance depending on the force applied to them. To provide information regarding joint angle, the rotational displacement and/or velocity of the input frame 136 with respect to the output frame 138 must be evaluated. This may be accomplished by, for example, placing a transparent window in the input frame 136 and illuminating with a light source a series of markers on an adjacent face of the output frame 138.

Figure 11:
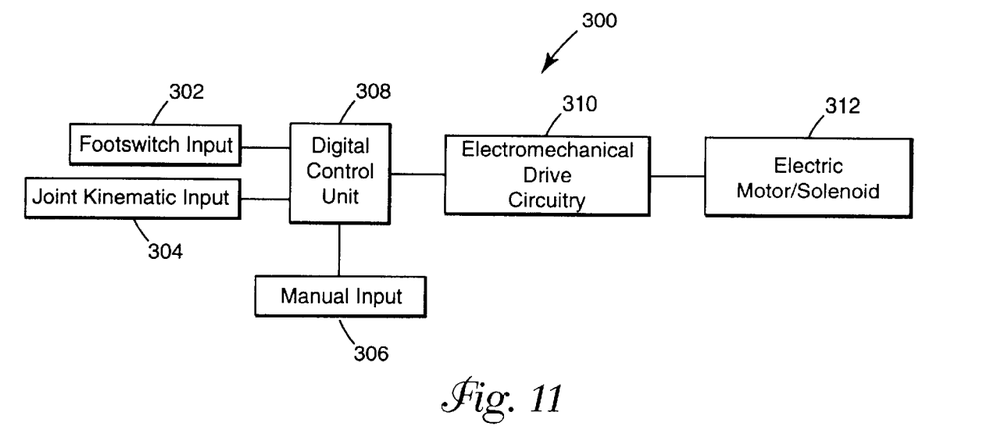
FIG. 11 is a schematic circuit diagram of the electronic control module of the invention.

Referring to FIG. 11, a basic circuit diagram of the solenoid control module circuitry 300 is illustrated. Electrical input signals 302 from an array of sensors on the second orthotic member 120, electrical input signals 304 regarding joint angle, and/or manual electrical input signals 306 from the wearer of the orthotic are provided to electronic circuitry such as, for example, a processor, in a digital control unit 308. For example, the wearer may wish to disengage the clutch manually before sitting down in a chair, or may wish to maintain disengagement while in a sitting position. Using these input signals, the processor provides electrical output signals to an electromechanical drive circuit 310. The drive circuit 310 then actuates the electric motor 312 in the solenoid 156 to disengage the clutch mechanism 134. The digital control unit 308 includes a battery or battery pack, which may be disposable or rechargeable, to power the circuitry 300.

Figure 12:
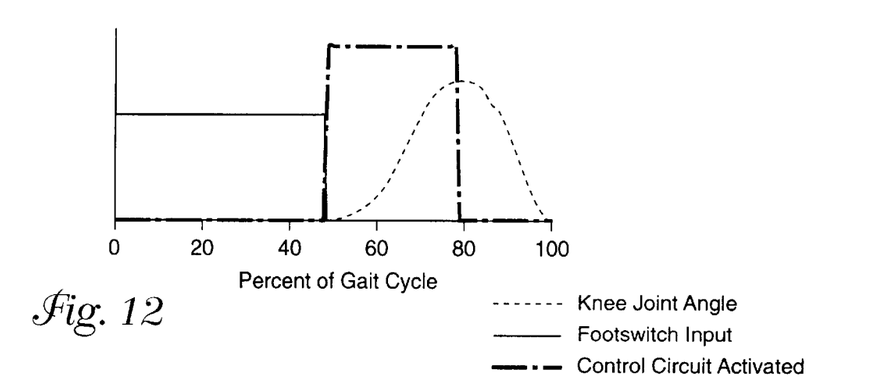
FIG. 12 is a plot showing activation of the solenoid vs. percent gait cycle.

Referring to FIG. 12, the operation of the closed loop control system of the invention to simulate the natural gait cycle is illustrated. The stance phase of the gait cycle in effect from 0 to about 60%, and the swing phase is in effect from about 60% to about 99%. The electrical input signals from the array of sensors on the second orthotic member signal weight transfer. The electrical output signals provided by a footswitch to the electronic control circuitry go to zero at about 50% gait cycle, in anticipation of swing phase. The solenoid is then activated, releasing the clutch and allowing the electromechanical knee joint to flex. Using the real time joint angle input, when the knee joint angle changes from positive (knee joint flexing) to negative (knee joint extending) the solenoid is deactivated (electrical output signals from the electronic control device go to zero). Knee joint extension is always possible due to the over running characteristics of the wrap spring clutch design.

The electronic control unit 308 and the electromechanical drive circuitry illustrated in FIG. 11 are typically contained within the electronic control module 158 (See FIG. 3). The electronic control module may also include a battery pack as a power source, or the battery pack may be a separate unit that plugs into the electronic control module. The batteries may be rechargeable or disposable. The electronic control module may be carried in, for example, a pouch worn at the wearer's waist, in a backpack, or may be attached to a strut on the orthotic device.

Figure 13:
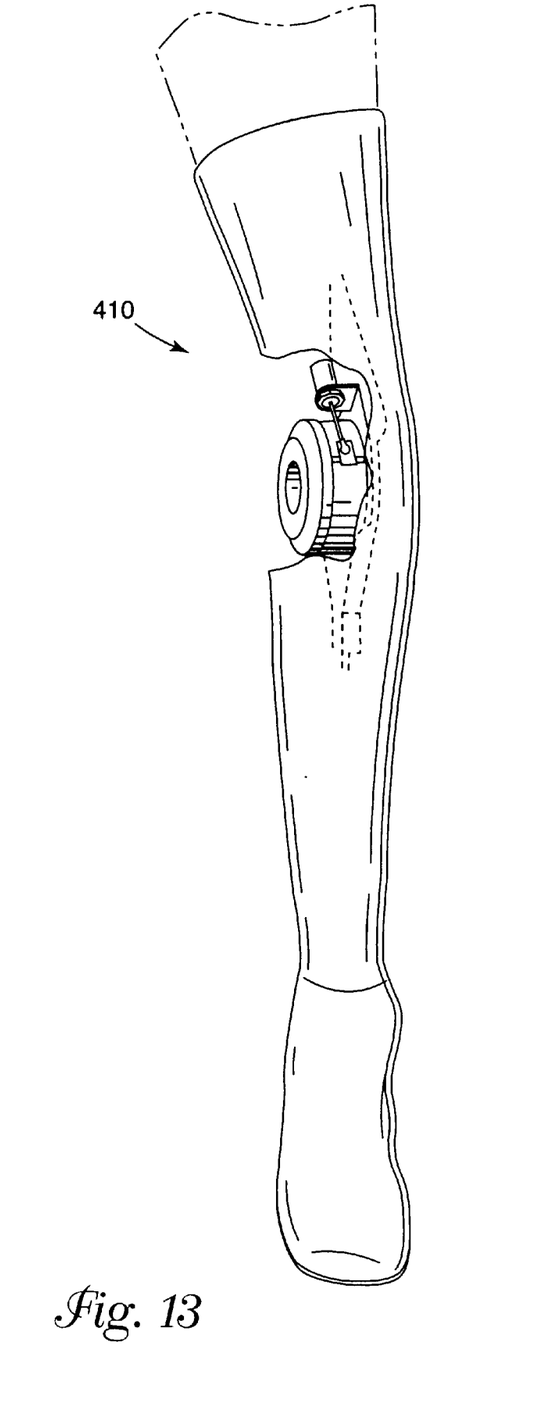
FIG. 13 is a schematic representation of the wrap spring clutch of the invention used in a prosthetic device.

The description of the invention above refers to orthotic devices, in which the lower extremities of the wearer are intact. However, as noted above, it should be understood that the invention may also be used as a prosthetic device for an amputee. For example, referring to FIG. 13, the clutch mechanism and the control system of the present invention may also be used an electromechanical replacement joint in a prosthetic device 410.

A number of embodiments of the invention have been described. Nevertheless, it will be understood that various modifications may be made without departing from the spirit and scope of the invention. For example, the joint control mechanism of the invention may be used to control other joints, such as the hip joint or the elbow joint. Accordingly, other embodiments are within the scope of the following claims.

What is claimed is:

1. A knee-ankle-foot orthotic device, comprising:
   (a) a medial thigh strut and a medial shank strut, wherein the medial thigh strut and the medial shank strut are attached at a hinge rotating about a flexion extension axis;
   (b) a lateral thigh strut and a lateral shank strut, wherein the lateral thigh strut and the lateral shank strut are attached to a wrap spring clutch rotating about the flexion extension axis, wherein the clutch comprises: an output frame attached to the lateral shank strut, wherein the output frame is attached to an output hub; an input frame attached to the lateral thigh strut, wherein the input frame is attached to an input hub, and the input hub further comprises an input shaft rotating within a bore in the output hub; and wherein the input frame and the output frame are adjacent to one another on a side of the clutch opposite the input hub;
   (c) a first orthotic member adapted to engage the thigh, wherein a medial side of the first orthotic member is attached to the medial thigh strut and a lateral side of the first orthotic member is attached to the lateral thigh strut;
   (d) a second orthotic member adapted to engage at least one of the lower limb and foot, wherein a medial side of the second orthotic member is attached to the medial shank strut and a lateral side of the second orthotic member is attached to the lateral shank strut;
   (e) an electrically actuated device attached to one of the first and second lateral struts, wherein said electrically activated device, when activated, disengages the clutch;
   (f) contact sensors attached to an underside of the second orthotic member, wherein the contact sensors generate an electrical signal corresponding to the degree of contact between the second orthotic member and a surface;
   (g) a kinematic sensor generating an electrical signal based on the relative position and/or movement of the input frame with respect to the output frame; and
   (h) an electronic control module receiving electrical input signals from the contact sensors and the kinematic sensors, and generating electrical output signals to actuate the electrically actuated device.

2. The device of claim 1, wherein the electronic control module further comprises a battery pack.

3. The device of claim 2, wherein the battery pack comprises batteries selected from disposable and rechargeable batteries.

4. The device of claim 1, wherein the electronic control module is housed in a pouch at the waist of the wearer.

5. The device of claim 1, wherein the electronic control module is attached to the orthotic device.

6. The device of claim 1, wherein the electronic control module receives manual electrical input and override signals from the wearer of the device and generates electrical output signals to control the electrically activated device.

7. The device of claim 1, wherein the clutch further comprises a spring engaging the input hub and the output hub, a circumferential spring clamp securing the spring to the input hub, and wherein the spring further comprises a control tang.

8. The device of claim 7, wherein the spring clamp comprises a tangential set screw.

9. The device of claim 7, further comprising a substantially cylindrical control collar on an outer surface of the spring, wherein the control collar engages the control tang on the spring.

10. The device of claim 8, wherein the control collar abuts the output frame and comprises a longitudinal slot, and the control tang is carried in the slot.

11. The device of claim 1, wherein the input frame and the output frame are substantially planar, and a plane of the input frame is substantially parallel to a plane of the output frame.

12. The device of claim 11, wherein a longitudinal axis of the input shaft is substantially normal to the plane of the input frame.

13. The device of claim 1, wherein the input shaft rotates in flanged sleeve bearings in the bore of the output hub, and a flange on a bearing resides between the input hub and the output hub.

14. The device of claim 1, wherein the input shaft comprises a longitudinal keyway.

15. The device of claim 14, wherein the input hub has an interior surface adjacent the input shaft, and the interior surface of the input hub comprises a notch to engage a key.

16. The device of claim 14, wherein the input hub further comprises a tangential screw.

17. The device of claim 1, wherein a first end of the input shaft extends beyond the output hub and the first end of the input shaft has an octagonal cross section.

18. The device of claim 17, wherein an interior surface of the input hub has an octagonal cross section to engage the first end of the input shaft.

19. The device of claim 1, wherein the output frame further comprises annular arcuate slots, and said arcuate slots engage a set screw on the input frame to limit the extent of relative rotation between the input frame and the output frame.

20. A knee-ankle-foot orthotic device, comprising:
(a) a medial thigh strut and a medial shank strut, wherein the medial thigh strut and the medial shank strut are attached at a hinge rotating about a flexion extension axis;
(b) a lateral thigh strut and a lateral shank strut, wherein the lateral thigh strut and the lateral shank strut are attached to a clutch, wherein said clutch rotates about the flexion/extension axis, and wherein the clutch comprises:
an output hub on an output frame attached to the lateral shank strut;
an input shaft on an input frame attached to the lateral thigh strut, wherein the input shaft rotates within a bore in the output hub;
an input hub on an end of the input shaft, wherein the input frame and the output frame are adjacent one another on a side of the clutch opposite the input hub;
a spring engaging the input hub and the output hub, wherein the spring comprises a control tang;
a substantially cylindrical control collar on an outer surface of the spring, wherein the control collar has an interior surface with a longitudinal slot engaging the control tang on the spring, and an exterior surface of the control collar comprising a yoke; and
a circumferential spring clamp securing the spring to the input hub;
(c) a first orthotic member adapted to engage the thigh, wherein a medial side of the first orthotic member is attached to the medial thigh strut and a lateral side of the first orthotic member is attached to the lateral thigh strut;
(d) a second orthotic member adapted to engage at least one of the lower limb and foot, wherein a medial side of the second orthotic member is attached to the medial shank strut and a lateral side of the second orthotic member is attached to the lateral shank strut;
(e) an electrically actuated solenoid attached to one of the first and second lateral struts, wherein said solenoid comprises an output shaft attached to the yoke on the control collar;
(f) contact sensors attached to the second orthotic member and acted upon by a walking surface, wherein the contact sensors generate an electrical signal corresponding to the degree of contact between the orthotic member and the surface;
(g) a kinematic sensor generating an electrical signal based on the relative position and/or movement of the input frame with respect to the output frame; and
(h) an electronic control module, wherein the module comprises electronic circuitry to receive electrical input signals from the contact sensors and the kinematic sensors, and generate electrical output signals to operate the solenoid.

21. A knee-ankle-foot orthotic device, comprising a lateral thigh strut and a lateral shank strut, wherein the lateral thigh strut and the lateral shank strut are attached to a wrap spring clutch rotating about a flexion extension axis, wherein the clutch comprises an output frame attached to the lateral shank strut, wherein the output frame is attached to an output hub; an input frame attached to the lateral thigh strut, wherein the input frame is attached to an input hub, and the input hub further comprises an input shaft rotating within a bore in the output hub; and wherein the input frame and the output frame are adjacent to one another on a side of the clutch opposite the input hub.

22. The device of claim 21, further comprising an electrically actuated device attached to one of the first and second lateral struts, wherein said electrically activated device, when activated, disengages the clutch.

23. The device of claim 22, further comprising a kinematic sensor generating an electrical signal based on the relative position and/or movement of the input frame with respect to the output frame.

24. The device of claim 21, wherein the clutch further comprises a spring engaging the input hub and the output hub, a circumferential spring clamp securing the spring to the input hub, and wherein the spring further comprises a control tang.

25. The device of claim 24, further comprising a substantially cylindrical control collar on an outer surface of the spring, wherein the control collar engages the control tang on the spring.

26. The device of claim 25, wherein the control collar abuts the output frame and comprises a longitudinal slot, and the control tang is carried in the slot.

27. The device of claim 24, wherein the spring clamp comprises a tangential screw.

28. The device of claim 21, wherein the input shaft rotates in flanged sleeve bearings in the bore of the output hub, and a flange on a bearing resides between the input hub and the output hub.

29. The device of claim 21, wherein the input shaft comprises a longitudinal keyway.

30. The device of claim 29, wherein the input hub has an interior surface adjacent to the input shaft, and the interior surface of the input hub comprises a notch to engage a key.

31. The device of claim 29, wherein the input hub further comprises a tangential screw.

32. The device of claim 21, wherein a first end of the input shaft extends beyond the output hub and the first end of the input shaft has an octagonal cross section.

33. The device of claim 32, wherein an interior surface of the input hub has an octagonal cross section to engage the first end of the input shaft.

* * * * *